United States Patent [19]

Alexander et al.

[11] Patent Number: 5,733,907
[45] Date of Patent: Mar. 31, 1998

[54] PRODRUGS OF AN INHIBITOR OF HIV PROTEASE

[75] Inventors: Jose Alexander; Dilbir Bindra, both of Lawrence,, Kans.; Bruce D. Dorsey, Harleysville, Pa.; Arnold J. Repta, Lawrence, Kans.; Joseph P. Vacca, Telford, Pa.

[73] Assignee: Merck & Co., Inc., Rahway, N.J.

[21] Appl. No.: 622,945

[22] Filed: Mar. 27, 1996

Related U.S. Application Data

[63] Continuation of Ser. No. 154,204, Nov. 18, 1993, abandoned.

[51] Int. Cl.$^6$ .............. A61K 31/495; A61K 31/535; C07D 401/06; C07D 413/14
[52] U.S. Cl. .............. 514/227.8; 514/235.8; 514/252; 544/60; 544/121; 544/357; 544/360; 544/364
[58] Field of Search .............. 544/360, 60, 121, 544/357, 364; 514/252, 227.8, 235.8

[56] References Cited

U.S. PATENT DOCUMENTS

| | | | |
|---|---|---|---|
| 3,950,333 | 4/1976 | Durant et al. | 544/310 |
| 4,144,346 | 3/1979 | Heeres et al. | 544/370 |
| 4,223,036 | 9/1980 | Heeres et al. | 544/370 |
| 4,661,473 | 4/1987 | Boger et al. | 514/16 |
| 5,132,400 | 7/1992 | Gammill et al. | 530/317 |
| 5,169,952 | 12/1992 | Askin et al. | 544/137 |
| 5,218,114 | 6/1993 | Bock et al. | 540/509 |
| 5,413,999 | 5/1995 | Vacca et al. | 544/360 |
| 5,455,351 | 10/1995 | Kempf et al. | 544/364 |
| 5,463,067 | 10/1995 | Askin et al. | 548/113 |
| 5,496,948 | 3/1996 | Askin et al. | 544/360 |
| 5,578,597 | 11/1996 | Spector et al. | 514/255 |

FOREIGN PATENT DOCUMENTS

| | | |
|---|---|---|
| 541168 | 5/1993 | European Pat. Off. . |
| 9008128 | 7/1990 | WIPO . |

OTHER PUBLICATIONS

Dean L. Winslow et al, AIDS, 1994, vol. 8, No. 6, pp. 753–756.
Plattner et al, J. Med. Chem. 1988, 31, 2277–2288.
Askin et al. J. Org Chem. 1992, 57, 2771–2773.
Saunders, "Drug Design and Discovery" 1992, vol. 8, pp. 255–263 (1992).
Saari et al. J. Med. Chem. 1992, 35, 3792–3802.
U.S. application No. 08/059,038, Merck, filed May 7, 1993.
U.S. application No. 08/092,627, Merck, filed Jul. 16, 1993

*Primary Examiner*—Emily Bernhardt
*Attorney, Agent, or Firm*—Mary A. Appollina; Jack L. Tribble

[57] ABSTRACT

Prodrugs of the HIV protease inhibitor L-735,524 are useful in the inhibition of HIV protease, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating ADS and methods of preventing or treating infection by HIV are also described.

5 Claims, No Drawings

PRODRUGS OF AN INHIBITOR OF HIV PROTEASE

This is a continuation of application Ser. No. 08/154,204 filed on Nov. 18, 1993, now abandoned.

BACKGROUND OF THE INVENTION

This case is related to Merck Case 18996, U.S. Ser. No. 08/059,038, filed May 7, 1993, and Merck Case 19097, U.S. Ser. No. 08/135,706, filed Oct. 13, 1993.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., Proc. Nat'l Acad. Sci. 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Rather, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compound L-735,524 is a potent inhibitor of HIV protease and is useful in the treatment of AIDS or ARC, without substantial side effects or toxicity.

Applicants have discovered prodrug forms of L-735,524, which are esters. These prodrugs afford improved delivery properties more consonant with extended release systems, and may improve intestinal absorption at extended times after oral dosing.

L-735,524 is not well absorbed in man beyond the first few hours post-oral dosing. Because of the short biological half-life, administration as an extended release dosage form would decrease dosing frequency. However, the very low aqueous solubility of the free base and the low pKa values (app. 3.7 and 5.9) of the protonated compound likely result in inadequate solubility in the ileum, jejunum, and colon where pH is usually greater than 6.0. By preparing more soluble prodrugs which afford improved solubility in the intestine and which revert to the parent in the intestine or revert during or subsequently to absorption, the barriers to formulation as a controlled release dosage form may be overcome.

BRIEF DESCRIPTION OF THE INVENTION

The prodrugs of this invention are useful in the inhibition of HIV protease, the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by H/V, and methods of treating infection by HIV are also disclosed.

DETAILED DESCRIPTION OF THE INVENTION AND PREFERRED EMBODIMENTS

This invention is concerned with the prodrugs of L-735, 524, or pharmaceutically acceptable salts thereof, in the inhibition of HIV protease, the prevention or treatment of infection by HIV and in the treatment of the resulting acquired immune deficiency syndrome (AIDS). The prodrugs are defined as follows:

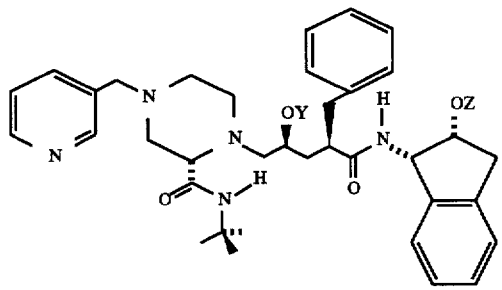

or pharmaceutically acceptable salts thereof,
wherein Y and Z are not both H, and
Y and Z are independently H;  (a)

$-C(=O)-(CR^1R^2)_n-COOR^3$;  (b)

$-C(=O)-(CR^1R^2)_nR^4$, except that Z is never $-C(=O)-C_{1-4}$ alkyl-$NH_2$; or  (c)

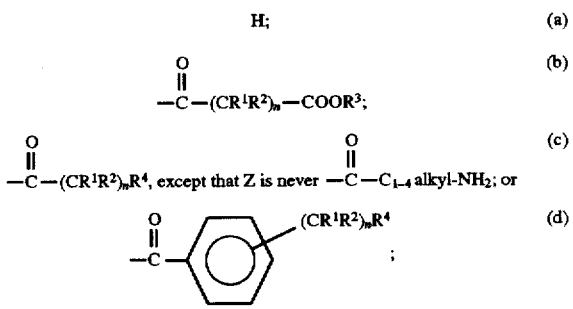  (d)

$n=0-16$;

$R^1$ and $R^2$ are independently H; hydroxy; amino; phenyl; heterocycle; or $C_{1-4}$ alkyl unsubstituted or substituted with hydroxy, —COOH, amino, aryl, keto, or heterocycle;

$C_3$ is H; or $C_{1-4}$ alkyl unsubstituted or substituted with aryl, amino,

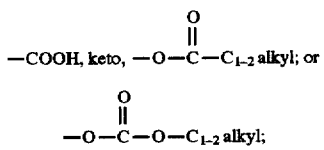

$R^4$ is H, $-NR^1R^2$, or heterocycle.

A presently preferred embodiment is a sodium, potassium, hydrochloride or sulfate salt, wherein at least one of Y or Z forms succinate, glutarate or adipate ester.

The HIV protease inhibitor L-735,524 is synthesized by the protocol of Merck Case 18597Y, EP 0541168, published 12 May 1993, herein incorporated by reference. The compound L-735,524 is N-(2(R)-hydroxy-1(S)-indanyl)-2(R)- phenylmethyl-4-(S)-hydroxy-5-(1-(4-(3-pyridylmethyl)-2 (S)-N'-(t-butylcarboxamido)-piperazinyl))-pentaneamide, or pharmaceutically acceptable salt thereof. Related synthetic background is contained in EP 0337714, hereby incorporated by reference for these purposes.

The prodrugs of this invention may also be combined with inhibitors of P450 cytochrome, such as ketoconazole or cimetidine. These inhibitors are useful in enhancing the lifetimes of the prodrug by inhibiting metabolic oxidation.

Ketoconazole is cis-1-acetyl-4-[4-[[2-(2,4-dichlorophenyl)-2-(1H-imidazol-1-ylmethyl)-1,3-dioxolan-4-yl]-methoxy]-phenyl]-piperazine or pharmaceutically acceptable salt thereof. It is synthesized by the procedures of U.S. Pat. No. 4,144,346 or U.S. Pat. No. 4,223,036, both incorporated by reference for these purposes.

Cimetidine is N-cyano-N'-methyl-N"-[2-[[(5-methyl-1H-imidazol-4-yl)methyl]thio]ethyl]guanidine, or pharmaceutically acceptable salt thereof. It is synthesized by the procedures of U.S. Pat. No. 3,950,333, incorporated by reference for this purpose.

The compounds of the present invention may have asymmetric or chiral centers and occur as racemates; racemic mixtures and as individual diastereomers or enantiomers, with all isomeric forms being included in the present invention.

When any variable (e.g., heterocycle, $R^1$ or $R^2$, etc.) occurs more than one time in any constituent its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge.

As used herein, with exceptions as noted, "aryl" is intended to mean phenyl (Ph) or naphthyl.

The term heterocycle or heterocyclic, as used herein except where noted, represents a stable 5- to 7-membered monocyclic heterocyclic ring which is saturated, and which consists of carbon atoms and from one to three heteroatoms selected from the group consisting of N or O or S. The heterocyclic ring must be attached at the N heteroatom where present. Examples of such heterocyclic elements include 4-morpholinyl, 1-piperazinyl, 1-piperidyl, 1-pyrrolidinyl, or 4-thiomorpholinyl.

The pharmaceutically-acceptable salts in the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, phosphate, pyrophosphate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Esterification of alcohols, such as L-735,524, is performed by a variety of conventional procedures, including reacting the alcohol group with the appropriate anhydride, carboxylic acid or acid chloride. These reactions, as well as other methods of esterification of alcohols, are readily apparent to the skilled artisan.

Reaction of the alcohol(s) with the appropriate anhydride (illustrated in Example 1) is carried out in the presence of an acylation catalyst, such as 4-DMAP (4-dimethylaminopyridine, also known as N,N-dimethylaminopyridine), or pyridine, or 1,8-bis [dimethylamino]-naphthalene. The preferred acylation catalyst is 4-DMAP.

Reaction of the alcohol with the appropriate carboxylic acid (illustrated in Example 2) is carried out in the presence of a dehydrating agent and, optionally, an acylation catalyst. The dehydrating agent, which serves to drive the reaction by the removal of water, is selected from dicyclohexylcarbodiimide (DDC), 1-[3-dimethylaminopropyl]-3-ethylcarbodiimide (EDC) or other water-soluble dehydrating agents. A preferred dehydrating agent is DDC.

Alternatively, reaction of the alcohol with appropriate carboxylic acid can also result in esterification, if performed instead in the presence of trifluoroacetic anhydride, and, optionally, pyridine. A further variant is reacting the alcohol with appropriate carboxylic acid in the presence of N,N-carbonyldiimidazole without pyridine.

Reaction of the alcohol with the acid chloride is carried out with an acylation catalyst, such as 4-DMAP or pyridine.

Selective esterification is performed by a variety of methods. In one preferred method illustrated by Examples 2 and 3, the alcohol is first esterified with a trichloroethyl derivative. After chromatographic isolation of the preferred ester, reductive elimination of the trichloroethyl group is carded out by reaction with zinc dust in acetic acid. Alternatively, another method of selective esterification is the hydrolysis of the bis-ester.

The compounds of the present invention are useful in the inhibition of HIV protease, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of each compound in the combination of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered to humans in the dosage ranges specific for each compound. L-735,524 or pharmaceutically acceptable salt thereof is administered orally in a dosage range between about 40 mg and about 4000 mg per day, divided into between one and four doses per day. Ketoconazole or pharmaceutically acceptable salt thereof is administered orally at a dosage range between about 200 mg every other day and about 400 mg twice a day. Cimetidine or pharmaceutically acceptable salt thereof is administered orally or i.v. at a dosage range between about 100 mg and about 4800 mg per day, divided into between one and four doses per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLE 1

N-[2(R)-Succinoyloxy-1(S)-indanyl-5-[[2(S)-t-butylaminocarbonyl]-4-(3-pyridylmethyl)piperazino]-4(S)-succinoyloxy-2(R)-phenylmethyl-pentaneamide (L-735,524 bis-succinate ester, L-751,368)

A solution of L-735,524 monohydrate (1.5 g) and succinic anhydride (2.5 g) in pyridine (10 mL) was stirred at room temperature for 24 hours. The pyridine was evaporated off on a rotary evaporator and the residue was dissolved in a mixture of water (30 mL) and chloroform (150 mL). The aqueous layer was removed and the organic layer was washed with water. The chloroform solution was dried over sodium sulfate and evaporated. The residue was vacuum dried overnight to furnish the pyridinium salt as a foamy solid that weighed 2.45 g. It was dissolved in acetic acid (25 mL) and the excess acetic acid was evaporated off on a rotary evaporator. The residue was vacuum dried to obtain a glassy solid. This was dissolved in ethanol (5 mL) and cooled in an ice bath. Ice cold water (50 mL) was added to the ethanol solution in small portions with vigorous stirring. The white precipitate that formed was whipped to a fine suspension using a magnetic stirrer. The precipitate was filtered, washed with water and vacuum dried to get the product as a white powder (1.7 g), which was homogenous by TLC and HPLC.

EXAMPLE 2

N-[2(R)-Trichloroethoxysuccinoyloxy-1(S)-indanyl-5-[[2(S)-t-butylamino carbonyl]-4-(3-pyridylmethyl)piperazino]-4(S)-hydroxy-2(R)-phenylmethyl-pentaneamide (L-735,524, trichloroethyl succinate monoester)

L-735,524 monohydrate (2.35 g), mono-trichloroethyl succinate (1.1 g), 4-dimethylaminnopyridine (0.49 g) and dicyclohexylcarbodiimide (0.9 g) were dissolved in chloroform (50 mL) and stirred at room temperature overnight. The reaction mixture was cooled in ice and the precipitated dicyclohexylurea was filtered off. The filtrate was acidified with 0.3 mL of acetic acid and washed twice with water and once with brine. The chloroform solution was evaporated to obtain a white foam (4.14 g) which consisted of a mixture of two isomeric monoesters, the di-ester, unreacted starting material and some dicyclohexylurea. This mixture was divided into four batches and purified by preparative TLC on silica gel plates. Using methanol-chloroform (8:92) as the developing solvent. The fractions enriched in the required monoester were combined and rechromatographed using methanol-chloroform (3:97) to get the pure trichloroethyl monosuccinate (1.85 g).

EXAMPLE 3

N-[2(R)-Succinoyloxy-1(S)-indanyl-5-[[2(S)-t-butylaminocarbonyl]-4-(3-pyridylmethyl)piperazino]-4(S)-hydroxy-2(R)-phenylmethyl-pentaneamide (L-735,524 monosuccinate ester, L-755,550)

The trichloroethyl ester of Example 2 (1.8 g) was dissolved in acetic acid (50 mL) and zinc dust (3 g) was added. After stirring for three hours at room temperature, an additional 1.5 g of zinc dust was added and stirring for was continued 3 more hours. The reaction mixture was filtered and the filtrate was evaporated. The residue was taken in chloroform (100 mL) and washed with water (2×50 mL) and brine. The chloroform solution was evaporated to furnish 1.34 g of a foamy solid. It was purified by preparative TLC on silica gel using methanol-chloroform (15:85) to obtain the pure monoester. It was dissolved in chloroform and filtered through a short bed of celite in a Pasteur pipet. Evaporation of chloroform gave the pure monoester as a white powder (1.23 g).

EXAMPLE 4

Protocol for Therapy with the Bis-Succinate Ester

In this protocol for HIV-seronegative subjects, the product of Example 1 is administered at a total daily dose of 500–1500 mg. Antiviral activity is measured before and during therapy by measuring serum levels of the HIV p24 antigen, serum levels of HIV RNA, and CD4 lymphocyte counts.

EXAMPLE 5

Protocol for Therapy with a Succinate Monoester

In this protocol for HIV-seronegative subjects, the product of Example 3 is administered at a total daily dose of 500–1500 mg. Antiviral activity is measured before and during therapy by measuring serum levels of the HIV p24 antigen, serum levels of HIV RNA, and CD4 lymphocyte counts.

EXAMPLE 6

Preparation of N-(2(R)-(dimethylamino acetoxy)-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide

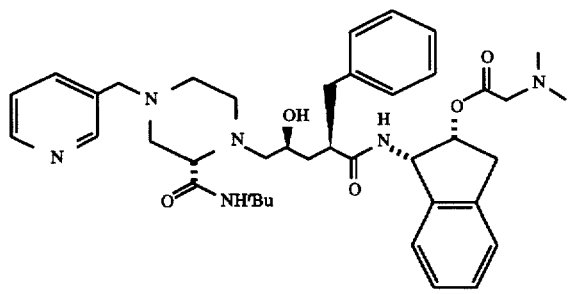

To a solution of N-(2(R)-hydroxy-1 (S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (700 mg, 1.109 mmol) dissolved in 4 mL of methylene chloride was added N,N-dimethyl-glycine (137 mg, 1.331 mmol), 1,3-dicyclohexylcarbodiimide (274 mg, 1.331 mmol) and a catalytic amount of N,N-dimethylaminopyridine (13 mg, 0.11 mmol). After 18 h at room temperature the reaction was filtered and concentrated to a white foam. The residue was purified via column chromatography (40×150 mm column, gradient elution $CH_2Cl_2$:$CHCl_3$ sat'd with $NH_3$: MeOH 60:39.5:0.5% (1000 mL), 60:39:1% (1000 mL), 60:38.5:1.5% (1000 mL). This provided 310 mg of a white foam which titrated with ethyl acetate: hexanes (20:80) to provide 215 mg of a white solid. mp 78°–82° C. Anal. Calcd for $C_{40}H_{54}N_6O_5$ 0.8 mol $H_2O$: C, 67.35; H, 7.86; N, 11.78 Found: C, 67.37; H, 7.67, N, 11.49.

EXAMPLE 7

The following compounds were prepared following the same conditions described in Example 6.

A. N-(2(R)-(benzoyloxy)-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide B. N-(2(R)-(nonoyloxy)-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide

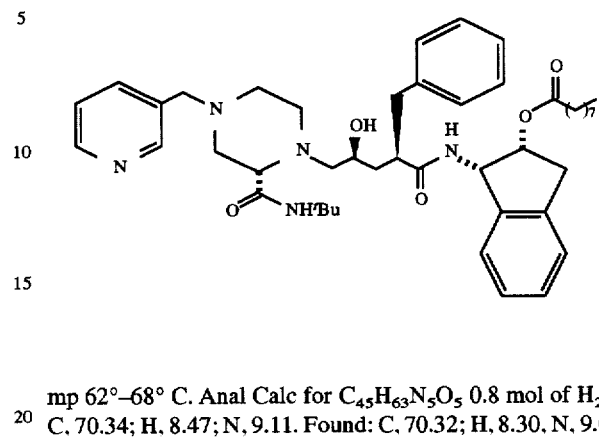

mp 62°–68° C. Anal Calc for $C_{45}H_{63}N_5O_5$ 0.8 mol of $H_2O$: C, 70.34; H, 8.47; N, 9.11. Found: C, 70.32; H, 8.30, N, 9.06.

C. N-(2(R)-(acetoxy)-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide

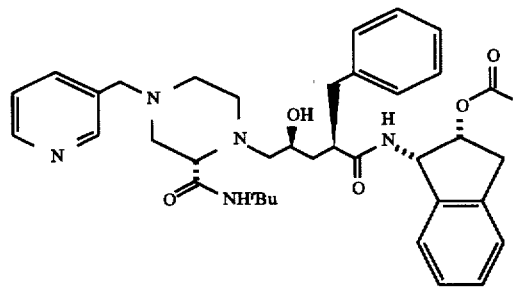

mp 90°–94° C. Anal. Calcd for $C_{38}H_{49}N_5O_5$ 0.4 mol of $CH_2Cl_2$: C, 66.86; H, 7.28; N, 10.15. Found: C, 66.77; H, 7.19, N, 10.44.

D. N-(2(R)-(acetoxy)-1(S)-indanyl)-2(R)-phenylmethyl-4(S)-(acetoxy)-5-(1-(4-(3-pyridylmethyl)-2(S)-N'-(t-butylcarboxamido)-piperazinyl))-pentaneamide

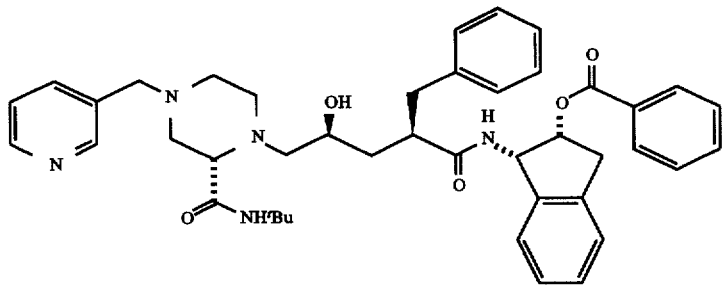

mp 154°–161° C. Anal. Calcd for $C_{43}H_{51}N_5O_5$: C, 71.94; H, 7.16; N, 9.76. Found: C, 71.93; H, 7.19, N, 9.76.

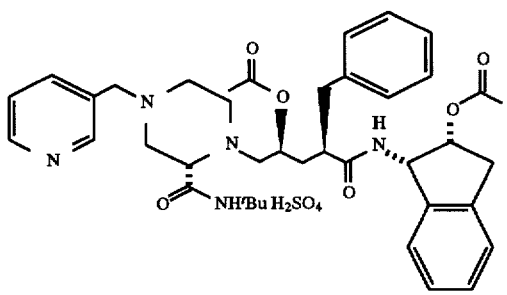

2.5 equivalents of all regeants were required for this bisacetate. After chromatography recovered an oil. Treated this oil with 1 equivalent of H$_2$SO$_4$ in ethyl acetate. Concentrated this solution to a white foam and dried under high vacuum (18 h, 55° C.). mp 133°–138° C. Anal. Calcd for C$_{40}$H$_{51}$N$_5$O$_6$ 1.35 mol of H$_2$SO$_4$: C, 58.21; H, 6.55; N, 8.48. Found: C, 58.12; H, 6.65, N, 8.20.

EXAMPLE 8

Preparation of N-(2(R)-((4-chloromethyl benzoyl)oxy)-1(S)-indanyl)-2(R)-phenylmethyl-4(S)-hydroxy-5-(1-(4-(3-pyridylmethyl)-2(S)-N '-(t-butylcarboxamido)-piperazinyl))-pentaneamide column, gradient elution CH$_2$Cl$_2$:CHCl$_3$ sat'd with NH$_3$: MeOH 60:39.5:0.0 (1000 mL), 60:39:1 (1000 mL), 60:38.5:1.5 (1000 mL), 60:38:2 (1000 mL), 60:37:3 (1000 mL), 60:35:5 (1000 mL). This provided 1.46 g of a white foam: tlc (CH$_2$Cl$_2$:CHCl$_3$ sat'd with NH$_3$: MeOH 60:35:5 Rf=0.26) $^1$H NMR (400 MHz, CDCl$_3$) δ 8.59–8.56 (m, 2H), 7.83–7.78 (m, 3H), 7.60 (m, 1H), 7.40 (d, J=12 Hz, 2H), 7.29–7.09 (m, 5H), 7.05–6.85 (m, 5H), 6.31 (d, J=8.3 Hz, 1H), 5.75 (dd, J=8.2 and 4.9 Hz, 1H), 5.50 (dd, J=4.7 and 4.03 Hz, 1H), 4.60 (s, 2H), 4.12 (br s, 1H), 3.89–3.83 (m, 1H), 3.51 (s, 2H), 3.29 (dd, J=17.5 and 4.0 Hz, 1H), 3.19–3.16 (m, 1H), 3.08 (d, 117.5 Hz, 1H), 2.95–2.91 (m, 1H), 2.83–2.45 (m, 8H), 2.38–2.29 (m, 1H), 1.90–1.81 (m, 1H), 1.62 (br s, 1H), 1.57–1.48 (m, 1H), 1.38 (s, 9H).

EXAMPLE 9

Preparation of N-(2(R)-((4-morpholinomethyl benzoyl)oxy)-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide

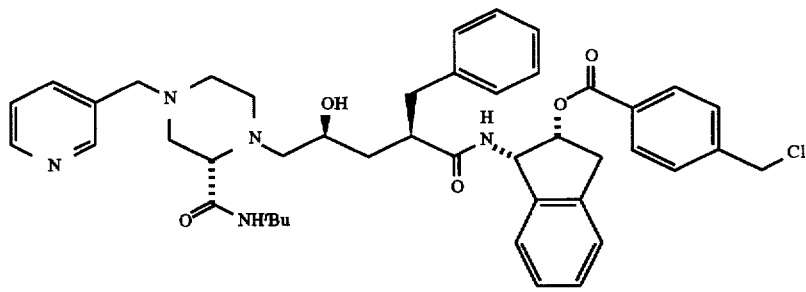

To a solution of N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (2.0

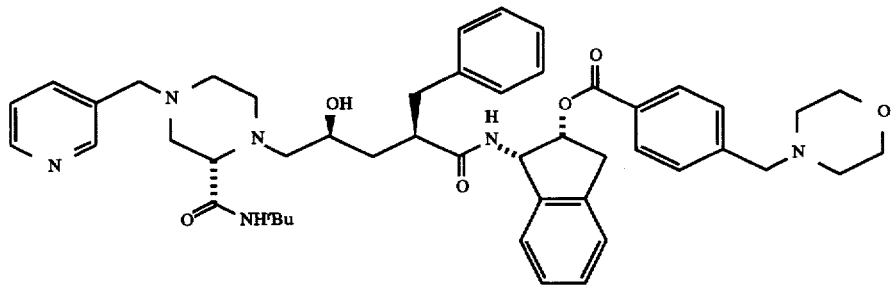

g, 3.16 mmol) dissolved in 20 mL of methylene chloride was added 4-chloromethyl benzoic acid (648 mg, 3.803 mmol), 1,3-dicyclohexylcarbodiimide (784 mg, 3.803 mmol) and a catalytic amount of N,N-dimethyaminopyridine s (38 mg, 0.317 mmol). After 24 h at room temperature the reaction was filtered and concentrated to a white foam. The residue was purified via column chromatography (50×150 mm To a solution of N-(2(R)-((4-chloromethyl benzoyl)oxy)-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (425 mg, 0.55 mmol) dissolved in I mL of anhydrous DMF was added morpholine (0.242 mL, 2.77 mmol). After 48 h the solution was diluted with 80 mL of ethyl acetate and washed with water (4×10 mL) and brine (1×10 mL), dried over MgSO₄, filtered and concentrated to a whim solid. Purification by flash column chromatography (40×150 mm column, gradient elution $CH_2Cl_2$:$CHCl_3$ sat'd with $NH_3$: MeOH 60:39.5:0.0 (1000 mL), 60:39:1 (1000 mL), 60:38.5:1.5 (1000 mL), 60:38:2 (1000 mL), 60:37:3 (1000 mL), 60:36:4 (1000 mL) provided 404 mg of a clear oil. Crystallization with ethyl acetate provided 350 mg of a white solid. mp 110°–120° C. Anal. Calcd for $C_{48}H_{60}N_6O_6$ 0.35 mol $H_2O$: C, 70.02; H, 7.43; N, 10.21. Found: C, 70.04; H, 7.34, N, 10.13.

EXAMPLE 10

Following the procedure described in Example 9 the following compounds were prepared.

A. N-(2(R)-4-((4'-methylpiperazine)methyl benzoyl)oxy-1(S)-indanyl)-2(R)-phenylmethyl-4(S)-hydroxy-5-(1-(4-(3-pyridylmethyl)-2(S)-N'-(t-butylcarboxamido)piperazinyl)-pentaneamide

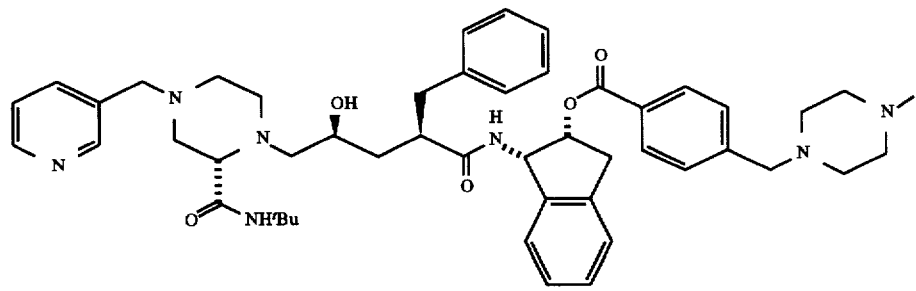

mp 88°–94° C. Anal. Calcd for $C_{49}H_{62}N_7O_5$ 1.0 mol $H_2O$: C, 69.48; H, 7.62; N, 11.57. Found: C, 69.33; H, 7.44, N, 11.35.

B. N-(2(R)-4-(N,N-diethylmethyl benzoyl)oxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide

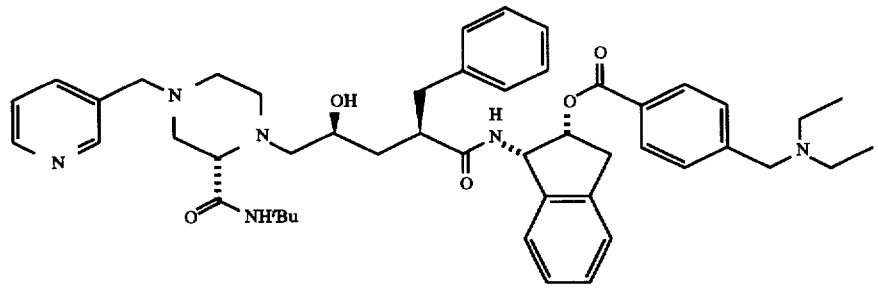

mp 135°–145° C. Anal. Calcd for $C_{48}H_{62}N_6O_5$ 0.4 mol $H_2O$: C, 71.15; H, 7.81; N, 10.37. Found: C, 71.11; H, 7.57, N, 10.77.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A prodrug of the formula

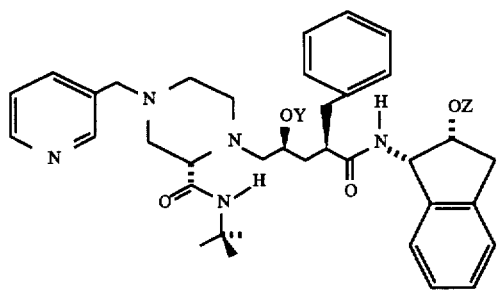

or pharmaceutically acceptable salts thereof, wherein Y and Z are not both H, and Y and Z are independently H;  (a)

$$\underset{\|}{\overset{O}{-C}}-(CR^1R^2)_n-COOR^3;$$  (b)

-continued $$\underset{\|}{\overset{O}{-C}}-(CR^1R^2)_nR^4, \text{ except that Z is never } \underset{\|}{\overset{O}{-C}}-C_{1-4}\text{ alkyl-}NH_2; \text{ or}$$  (c)

(d)

$$\underset{\|}{\overset{O}{-C}}\!\!-\!\!\!\bigcirc\!\!\!-\!\!(CR^1R^2)_nR^4 ;$$

n=0–16;

$R^1$ and $R^2$ are independently H; hydroxy; amino; phenyl; heterocycle; or $C_{1-4}$ alkyl unsubstituted or substituted with hydroxy, —COOH, amino, aryl, keto, or heterocycle;

$C_3$ is H; or $C_{1-4}$ alkyl unsubsidized or substituted with aryl, amino,

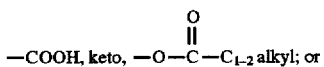

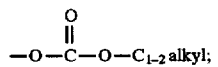

$R^4$ is H, —$NR_1R^2$, or heterocycle; and heterocycle is selected from 4-morpholinyl, 1-piperazinyl, 1-piperidyl, 1-pyrrolidinyl, or 4-thiomorpholinyl.

2. The prodrug of claim 1, wherein the pharmaceutically acceptable salt is sodium, potassium, hydrochloride or sulfate salt, and at least one of Y or Z forms a succinate, glutarate or adipate ester.

3. A method of inhibiting HIV protease, comprising administering to suitable mammal in need of such treatment an effective amount of the prodrug of claim 1.

4. A method of treating infection by HIV or of treating AIDS or ARC, comprising administering to a suitable mammal in need of such treatment an effective amount of the prodrug of claim 1.

5. A pharmaceutical composition comprising an effective amount of the prodrug of claim 1, and a pharmaceutically acceptable carrier.

* * * * *